United States Patent [19]

Di Giorgio et al.

[11] Patent Number: Plant 7,123

[45] Date of Patent: Jan. 23, 1990

[54] CARNATION NAMED DIGIDIA

[75] Inventors: Antonio Di Giorgio; Renato Di Giorgio, both of San Remo, Italy

[73] Assignee: Laboratoire de Physiologie Vegetale, La Londe, France

[21] Appl. No.: 295,460

[22] Filed: Jan. 10, 1989

[51] Int. Cl.[4] ..... A01H 5/00

[52] U.S. Cl. ..... Plt./70

[58] Field of Search ..... Plt./70

*Primary Examiner*—Robert E. Bagwill

*Attorney, Agent, or Firm*—Charles W. Rummler

[57] ABSTRACT

A new carnation variety particularly distinguished by its very large cream white flowers which are produced profusely at recurrent intervals during the Spring, Mid-season and Fall flowering periods, on very long, strong stems, the plant, having a height of about 130 cm. at eight months of growth. The flowers are borne singly on erect, rigid stems of a plant having a vigorous, upright growth habit with moderately abundant foliage and a well branched habit.

1 Drawing Sheet

BACKGROUND OF THE NEW PLANT

This new carnation variety originated as a mutation of a standard carnation plant named Chantal, a seedling originated by us at our nursery at San Remo, Italy and, this sport was discovered in 1986. It was particularly noted because of its very large white blossoms and because of this character this sport was asexually reproduced under our direction by means of cuttings at San Remo and propagation of a newly discovered plant was so successful that we carried on the propagation through several successive generations, by means of cuttings, at our San Remo nursery to determine whether its distinctive characteristics would hold true from generation to generation. This we found to be quite true and gave us the assurance that its homogeneity would be constant and adequately support propagation of the new plant on a commercial scale which is now being done at Laboratoire de Physiologie Vegetale, 83250 La Londe-Les Maures, France.

DESCRIPTION OF THE DRAWING

This new carnation cultivar is illustrated by the accompanying photographic drawing which shows several blooming stems including flowers at various stages of maturity with one of the stems showing a bud just prior to its bursting into a full flower, the color rendition shown being as nearly true to that herein specified as is reasonably possible to obtain by professional photographic procedures.

DESCRIPTION OF THE NEW PLANT

The following is a detailed description of our new standard carnation cultivar based upon observation of plants grown in greenhouse, as well as out of doors, at our nursery at San Remo, Italy, as well as at the nursery of Laboratoire de Physiologie Vegetale maintained at 83250 La Londe-Les Maures, France, the color designation stated herein being according to The R.H.S. Colour Chart published by The Royal Horticultural Society of London, England.

THE PLANT

Origin: Sport.

Parentage: The standard carnation variety named Chantal (unpatented).

Classification:

*Botanic.*—*Dianthus caryophyllus.*

*Commercial.*—Standard Carnation.

Form: A strong erect bush having at least four stems emitted near the ground.

Height: Averaging about 130 cm. at eight months of growth.

Main stem:

*Length.*—Less than 15 cm. due to pinching.

Growth habit: Vigorous, upright and rigid.

Branching character: This plant is well branched.

Foliage:

*Quantity.*—Moderately abundant.

*Number of leaves.*—More than 120.

*Leaf size.*—In average, about 13 cm. long and 0.85 cm. wide.

*Leaf shape.*—Oblong downwardly curved and with entire margins.

*Texture.*—Leathery.

*Color.*—Upper side and under side, 139-A.

*Ribs and veins.*—Hardly noticeable.

*Rachis.*—Hardly noticeable.

Flower stem:

*Length.*—About 78 cm.

*Character.*—Upright with good strength.

*Color.*—139-A.

THE BUD

Size: Large.

*Diameter.*—In average, about 2.3 cm.

*Length.*—In average, about 2.7 cm.

Shape: Ovoid.

Rate of opening: Normal.

Color of petals:

*When sepals first divide and when petals begin to unfurl.*—Creamy white.

Sepals:

*Number.*—Six.

*Shape.*—Ovoid with acute tip and joined together at the bottom ends.

*Character.*—The sepals are hooded over the bud and stand up when the flowers open.

*Color.*—Inside, 149-D. Outside, 143-B/143-C.

*Striae.*—Longitudinal.

Calyx:

*Size.*—Broad.

*Shape.*—Funnel-shaped.
*Splitting.*—A little splitting sometimes occurs.
*Aspect.*—Smooth.

Flower stem:
*Length.*—About 78 cm. (cut at the tenth node).
*Character.*—Rigid and erect.
*Color.*—139-A.

THE FLOWER

Blooming habit: Recurrent and profusely during the Spring, Midseason and Fall blooming periods.

Size of flower: Very large.
*Diameter.*—Averages about 8.5 cm.
*Depth.*—Averages about 6 cm.

Borne: Singly.

Shape: When bloom first opens, a high center. When bloom matures, dome shaped.

Petalage:
*Number of petals.*—In average, about 87.
*Arrangement.*—Imbricated.
*Form.*—Fan-shaped with all margins serrated.
*Appearance.*—Satiny.
*Color.*—All petals, top side and reverse side: Body — 155-D. Base — Greenish White.

Petaloids:
*Number.*—Less than 7.
*Size.*—Smaller than the petals.
*Color.*—Same as the petals.

Discoloration after full bloom: None.

Persistence: The flowers hang on and dry.

Fragrance: Perceptible.

Lasting quality: As a cut flower, at least ten days in vase keeping.

THE REPRODUCTIVE ORGANS

Stamens:
*Number.*—Two to six.
*Arrangement.*—Around the ovary.
*Anthers.*—Size: Less than 4 mm.

Pistils:
*Number.*—Four.
*Styles.*—Length: About 1.4 cm. Color: Whitish.
*Stigmas.*—Color: Whitish.

Character of ovaries: Ribbed.

This new carnation cultivar most nearly resembles its original plant, Chantal. However, it differs from Chantal in that it has a creamy white color whereas Chantal is of a Venetian pink color.

We claim:

1. A new and distinctive carnation plant, substantially as herein shown and described, particularly characterized by the very large size of its flower and the creamy white flower coloration, the blooms being grown on long, strong, upright stems and being produced profusely during its recurrent blooming seasons.

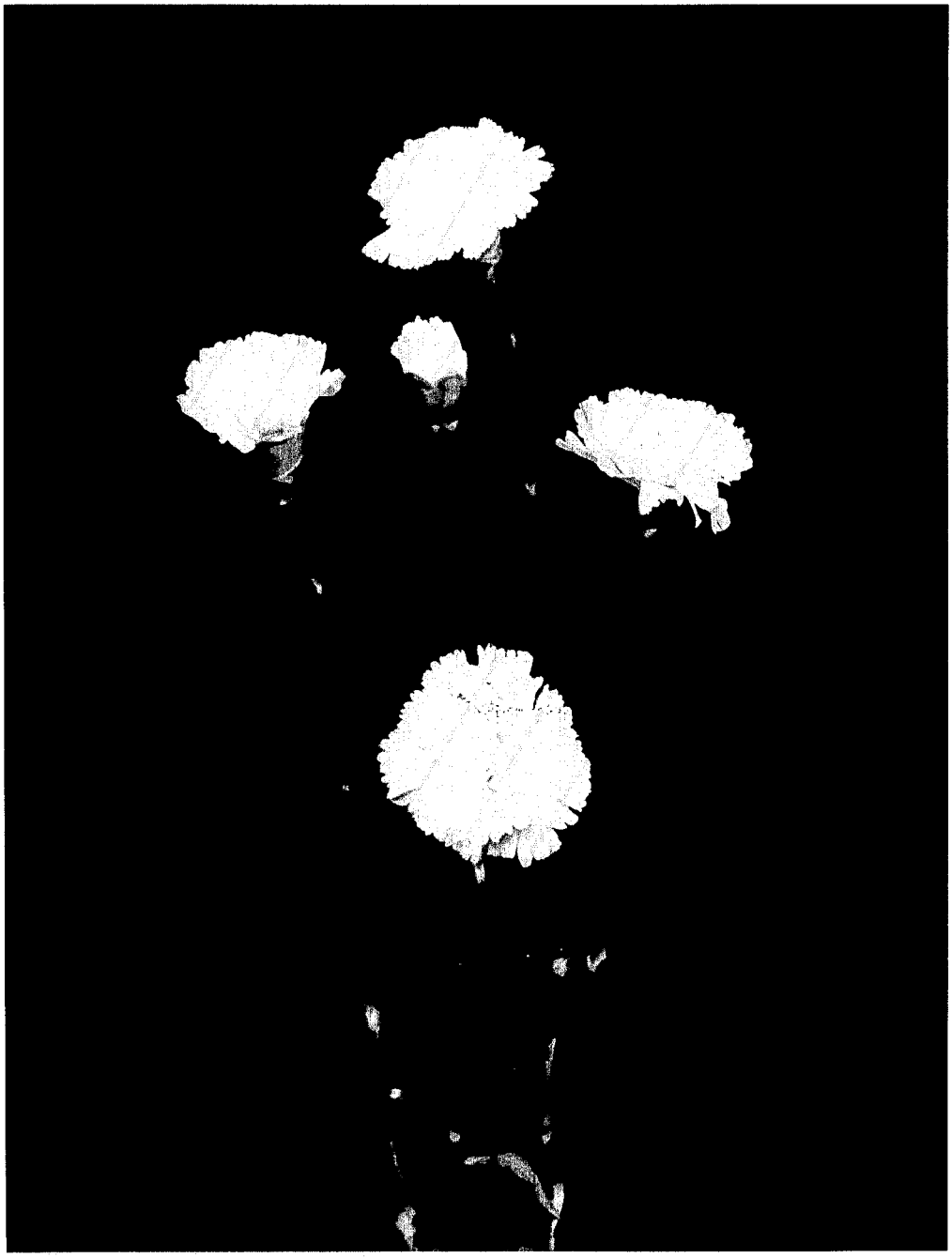

* * * * *